(12) United States Patent
Angros (10) Patent No.: US 9,464,974 B2
(45) Date of Patent: *Oct. 11, 2016

(54) IN SITU HEAT INDUCED ANTIGEN RECOVERY AND STAINING APPARATUS AND METHOD

(71) Applicant: Lee H. Angros, Bethany, OK (US)

(72) Inventor: Lee H. Angros, Bethany, OK (US)

(\*) Notice: Subject to any disclaimer, the term of this patent is extended or adjusted under 35 U.S.C. 154(b) by 171 days.

This patent is subject to a terminal disclaimer.

(21) Appl. No.: 14/253,555

(22) Filed: Apr. 15, 2014

(65) Prior Publication Data

US 2014/0227714 A1 Aug. 14, 2014

Related U.S. Application Data

(63) Continuation of application No. 13/742,174, filed on Jan. 15, 2013, now Pat. No. 8,696,988, which is a continuation of application No. 13/311,066, filed on Dec. 5, 2011, now Pat. No. 8,354,058, which is a (Continued)

(51) Int. Cl.
*G01N 33/543* (2006.01)
*G01N 1/44* (2006.01)

(Continued)

(52) U.S. Cl.
CPC ...... *G01N 1/44* (2013.01); *G01N 1/30* (2013.01); *G01N 1/312* (2013.01); *G01N 33/52* (2013.01); *G01N 33/521* (2013.01); *G01N 33/53* (2013.01);

(Continued)

(58) Field of Classification Search
CPC .... G01N 1/312; G01N 33/52; G01N 33/521; G01N 1/30; G01N 1/44; B01L 9/52; Y10T 436/11; Y10T 436/110833; Y10T 436/111666; Y10T 436/112499; Y10T 436/114165; Y10T 436/114998; Y10T 436/119163; Y10T 436/25; Y10T 436/2575

USPC .................................................... 436/501
See application file for complete search history.

(56) References Cited

U.S. PATENT DOCUMENTS 3,645,690 A 2/1972 Rochte et al.
4,296,070 A 10/1981 Montalto et al.
(Continued)

FOREIGN PATENT DOCUMENTS

EP 402994 A 12/1990
EP 0947135 4/2005
(Continued)

OTHER PUBLICATIONS

U.S. Appl. No. 60/076,198, Ford et al., filed Feb. 27, 1998.
U.S. Appl. No. 60/142,789, Angros, filed Jul. 8, 1999.
U.S. Appl. No. 60/375,679, Lemme et al., filed Apr. 26, 2002.
"Automated Systems" Brochure, BioGenex 2000.
"Dako® Autostainer Universal Staining System," Brochure, DAKO Corporation, 1999.
(Continued)

*Primary Examiner* — Mark Shibuya
*Assistant Examiner* — Pensee Do
(74) *Attorney, Agent, or Firm* — Dunlap Codding, P.C.

(57) ABSTRACT

An automated in situ heat induced antigen recovery and staining method and apparatus for treating a plurality of microscope slides. The process of heat induced antigen recovery and the process of staining the biological sample on the microscope slide are conducted in the same apparatus, wherein the microscope slides do not need to be physically removed from one apparatus to another. Each treatment step occurs within the same reaction compartment. The reaction conditions of each reaction compartment for treating a slide can preferably be controlled independently, including the individualized application of reagents to each slide and the individualized treatment of each slide.

40 Claims, 6 Drawing Sheets

Related U.S. Application Data continuation of application No. 12/624,120, filed on Nov. 23, 2009, now Pat. No. 8,071,023, which is a continuation of application No. 10/943,394, filed on Sep. 17, 2004, now Pat. No. 7,632,461, which is a continuation of application No. 10/388,710, filed on Mar. 14, 2003, now Pat. No. 6,855,292, which is a continuation of application No. 09/612,605, filed on Jul. 7, 2000, now Pat. No. 6,534,008.

(60) Provisional application No. 60/142,789, filed on Jul. 8, 1999.

(51) Int. Cl.
G01N 1/31 (2006.01)
G01N 33/52 (2006.01)
G01N 33/53 (2006.01)
G01N 1/30 (2006.01)
B01L 9/00 (2006.01)

(52) U.S. Cl.
CPC ............ G01N 33/5306 (2013.01); B01L 9/52 (2013.01); Y10T 436/11 (2015.01); Y10T 436/110833 (2015.01); Y10T 436/111666 (2015.01); Y10T 436/112499 (2015.01); Y10T 436/114165 (2015.01); Y10T 436/114998 (2015.01); Y10T 436/119163 (2015.01); Y10T 436/25 (2015.01); Y10T 436/2575 (2015.01)

(56) References Cited

U.S. PATENT DOCUMENTS

| | | |
|---|---|---|
| 4,847,208 A | 7/1989 | Bogen |
| 4,855,109 A | 8/1989 | Muraishi et al. |
| 4,857,272 A | 8/1989 | Sugaya |
| 5,073,504 A | 12/1991 | Bogen |
| 5,154,889 A | 10/1992 | Muraishi |
| 5,225,325 A | 7/1993 | Miller et al. |
| 5,232,664 A | 8/1993 | Krawzak et al. |
| 5,244,787 A | 9/1993 | Key et al. |
| 5,250,262 A | 10/1993 | Heidt et al. |
| 5,273,905 A | 12/1993 | Muller et al. |
| 5,316,452 A | 5/1994 | Bogen et al. |
| 5,355,439 A | 10/1994 | Bernstein et al. |
| 5,356,595 A | 10/1994 | Kanamori et al. |
| 5,425,918 A | 6/1995 | Healey et al. |
| 5,439,649 A | 8/1995 | Tseung et al. |
| 5,525,514 A | 6/1996 | Jacobs et al. |
| 5,551,487 A | 9/1996 | Gordon et al. |
| 5,578,452 A | 11/1996 | Shi et al. |
| 5,595,707 A | 1/1997 | Copeland et al. |
| 5,645,114 A | 7/1997 | Bogen et al. |
| 5,650,327 A | 7/1997 | Copeland et al. |
| 5,654,199 A | 8/1997 | Copeland et al. |
| 5,654,200 A | 8/1997 | Copeland et al. |
| 5,675,715 A | 10/1997 | Bernstein et al. |
| 5,696,887 A | 12/1997 | Bernstein et al. |
| 5,737,499 A | 4/1998 | Bernstein et al. |
| 5,758,033 A | 5/1998 | Bernstein et al. |
| 5,804,141 A | 9/1998 | Chianese |
| 5,819,842 A | 10/1998 | Potter |
| 5,839,091 A | 11/1998 | Rhett et al. |
| 5,882,601 A | 3/1999 | Kath et al. |
| 5,922,604 A | 7/1999 | Stapleton et al. |
| 5,947,167 A | 9/1999 | Bogen et al. |
| 5,948,359 A | 9/1999 | Kalra et al. |
| 5,958,341 A | 9/1999 | Chu |
| 5,985,669 A | 11/1999 | Palander |
| 6,093,574 A | 7/2000 | Druyor-Sanchez et al. |
| 6,096,271 A | 8/2000 | Bogen et al. |
| 6,180,061 B1 | 1/2001 | Bogen et al. |
| 6,183,693 B1 | 2/2001 | Bogen et al. |
| 6,207,408 B1 | 3/2001 | Essenfeld et al. |
| 6,218,191 B1 | 4/2001 | Palander |
| 6,269,846 B1 | 8/2001 | Overbeck et al. |
| 6,296,809 B1 | 10/2001 | Richards et al. |
| 6,352,861 B1 | 3/2002 | Copeland |
| 6,358,473 B1 | 3/2002 | Coello et al. |
| 6,403,036 B1 | 6/2002 | Rodgers et al. |
| 6,403,931 B1 | 6/2002 | Showalter et al. |
| 6,451,551 B1 | 9/2002 | Zhan et al. |
| 6,472,217 B1 | 10/2002 | Richards et al. |
| 6,489,171 B1 | 12/2002 | Aghassi et al. |
| 6,495,106 B1 | 12/2002 | Kalra et al. |
| 6,534,008 B1 | 3/2003 | Angros |
| 6,541,261 B1 | 4/2003 | Bogen |
| 6,544,798 B1 | 4/2003 | Christensen et al. |
| 6,582,962 B1 | 6/2003 | Richards et al. |
| 6,594,537 B1 | 7/2003 | Bernstein et al. |
| 6,632,598 B1 | 10/2003 | Zhang et al. |
| 6,638,770 B1 | 10/2003 | Montagu |
| 6,649,368 B1 | 11/2003 | Aghassi et al. |
| 6,673,620 B1 | 1/2004 | Loeffler et al. |
| 6,678,577 B1 | 1/2004 | Stylli et al. |
| D495,425 S | 8/2004 | Goris et al. |
| 6,783,733 B2 | 8/2004 | Bogen et al. |
| 6,827,901 B2 | 12/2004 | Copeland et al. |
| 6,855,292 B2 | 2/2005 | Angros |
| 6,855,559 B1 | 2/2005 | Christensen et al. |
| 6,930,292 B1 | 8/2005 | Winther et al. |
| 6,943,029 B2 | 9/2005 | Copeland et al. |
| 6,943,035 B1 | 9/2005 | Davies et al. |
| 7,025,933 B2 | 4/2006 | Ganz et al. |
| 7,250,301 B2 | 7/2007 | Angros |
| 7,318,913 B2 | 1/2008 | Loeffler et al. |
| 7,476,362 B2 | 1/2009 | Angros |
| 7,622,077 B2 | 11/2009 | Angros |
| 7,632,461 B2 | 12/2009 | Angros |
| 7,875,242 B2 | 1/2011 | Shah |
| 8,007,720 B2 | 8/2011 | Angros |
| 8,007,721 B2 | 8/2011 | Angros |
| 8,052,927 B2 | 11/2011 | Angros |
| 8,071,023 B2 | 12/2011 | Angros |
| 8,092,742 B2 | 1/2012 | Angros |
| 8,313,694 B2 | 11/2012 | Angros |
| 8,329,100 B2 | 12/2012 | Angros |
| 8,354,058 B2 | 1/2013 | Angros |
| 2003/0022391 A1 | 1/2003 | Richards et al. |
| 2003/0124729 A1 | 7/2003 | Christensen et al. |
| 2003/0203493 A1 | 10/2003 | Lemme et al. |
| 2003/0211630 A1 | 11/2003 | Richards et al. |
| 2004/0002163 A1 | 1/2004 | Reinhardt et al. |
| 2006/0188396 A1 | 8/2006 | Bedingham et al. |

FOREIGN PATENT DOCUMENTS

| | | |
|---|---|---|
| WO | WO 99/34190 | 7/1999 |
| WO | 9944030 | 9/1999 |
| WO | WO 00/14507 | 3/2000 |
| WO | PCT/US00/18686 | 11/2000 |
| WO | WO 01/07890 | 2/2001 |

OTHER PUBLICATIONS

"Declere™, One Giant Step Towards Standardization of IHC," Brochure, Cell Marque, 1999.
"Expanding the Power of NexES®", Ventana Brochure, 1998.
"Mark 5 HSS" Promotional Release and Flyer, Diagnostic Products Corporation, 1999.
"MISHA™" Catalog pp. 2-3, Shandon Lipshaw, 1997.
"One Platform. Infinite Possibilities™."Artisan Staining System Brochure, CytoLogix Corporation, 1999.
Pileri et al., "Antigen Retrieval Techniques in Immunohistochemistry: Comparison of Different Methods", Journal of Pathology, vol. 183, pp. 116-123 (1997).
"Protocol™ MicroProbe® Staining System for Immunohistochemistry and Special Stains," Fisher Healthcare Brochure, 1998.
Shi et al., "Antigen Retrieval Immunohistochemistry: Past, Present, and Future," J. of Histochemistry & Cytochemistry, 45I3):327-343, 1997.

(56) References Cited

OTHER PUBLICATIONS

Shi et al., "Development of an Optimal Protocol for Antigen Retrieval: A 'Test Batter' Approach Exemplified with Reference to the Staining of Retinoblastoma Protein (pRB) in Formalin-Fixed Paraffin Sections," J. of Pathology, 179:347-952, 1996.
Shi et al., "Use of pH 9.5 Tris-HCl Buffer Containing 5% Urea for Antigen Retrieval Immunohistochemistry," Biotechnic & Histochemistry, 71(4):190-195, 1996.
Taylor et al., "Comparative Study of Antigen Retrieval Heating Methods: Microwave, Microwave and Pressure cooker, Autoclave and Steamer," Biotechnic & Histochemistry, 71(5):263-270, 1996.
"TST Stainer Trio" Brochure, Mopec™,—dated prior to 1998.
"Walk-Away Automation for Special Stains and IHC" Brochure, CytoLogix Corporation,—dated prior to 1998.
"Zymed®" Immunohistopathology Catalog, Zymed Laboratories Inc., 1998-1999.
U.S. Appl. No. 09/612,605, Angros, Office Action Restriction dated Sep. 25, 2001.
U.S. Appl. No. 09/612,605, Angros, Response to Office Action Restriction filed Oct. 12, 2001.
U.S. Appl. No. 09/612,605, Angros, Notice of Allowance dated Jun. 10, 2002.
U.S. Appl. No. 09/612,605, Angros, Communication dated Jul. 12, 2002.
U.S. Appl. No. 10/245,035, Angros, Office Action Restriction dated Jan. 28, 2004.
U.S. Appl. No. 10/245,035, Angros, Response to Office Action Restriction filed Apr. 28, 2004.
U.S. Appl. No. 10/245,035, Angros, Office Action Restriction dated Jul. 27, 2004.
U.S. Appl. No. 10/245,035, Angros, Response to Office Action Restriction filed Sep. 17, 2004.
U.S. Appl. No. 10/245,035, Angros, Supplemental Preliminary Amendment filed Nov. 10, 2004.
U.S. Appl. No. 10/245,035, Angros, Office Action dated Jan. 26, 2005.
U.S. Appl. No. 10/245,035, Angros, Response to Office Action filed May 24, 2005.
U.S. Appl. No. 10/245,035, Angros, Supplemental Amendment filed Aug. 2, 2005.
U.S. Appl. No. 10/245,035, Angros, Final Office Action dated Jan. 19, 2006.
U.S. Appl. No. 10/245,035, Angros, Amendment and Request for Continued Exam filed Jun. 7, 2006.
U.S. Appl. No. 10/245,035, Angros, Supplemental Amendment filed Aug. 3, 2006.
U.S. Appl. No. 10/245,035, Angros, Second Supplemental Amendment filed Sep. 27, 2006.
U.S. Appl. No. 10/245,035, Angros, Third Supplemental Amendment filed Dec. 8, 2006.
U.S. Appl. No. 10/245,035, Angros, Interview Summary dated Jan. 11, 2007.
U.S. Appl. No. 10/245,035, Angros, Response to Interview Summary filed Jan. 29, 2007.
U.S. Appl. No. 10/245,035, Angros, Notice of Allowance dated Mar. 15, 2007.
U.S. Appl. No. 10/388,710, Angros, Office Action dated Mar. 18, 2004.
U.S. Appl. No. 10/388,710, Angros, Response to Office Action filed May 6, 2004.
U.S. Appl. No. 10/388,710, Angros, Notice of Allowance dated Jun. 15, 2004.
U.S. Appl. No. 10/388,710, Angros, Amendment after allowance dated Aug. 27, 2004.
U.S. Appl. No. 10/943,386, Angros, Office Action Restriction dated Apr. 9, 2007.
U.S. Appl. No. 10/943,386, Angros, Response to Election and Amendment filed Jul. 9, 2007.
U.S. Appl. No. 10/943,386, Angros, Second Preliminary Amendment filed Sep. 5, 2007.
U.S. Appl. No. 10/943,386, Angros, Office Action dated Nov. 1, 2007.
U.S. Appl. No. 10/943,386, Angros, Response to Office Action filed Nov. 19, 2007.
U.S. Appl. No. 10/943,386, Angros, Office Action dated Feb. 22, 2008.
U.S. Appl. No. 10/943,386, Angros, Response to Office Action filed May 30, 2008.
U.S. Appl. No. 10/943,386, Angros, Second Amendment and Response to Office Action filed Aug. 15, 2008.
U.S. Appl. No. 10/943,386, Angros, Office Action Restriction dated Apr. 27, 2009.
U.S. Appl. No. 10/943,386, Angros, Amendment and Response to Office Action filed Jun. 26, 2009.
U.S. Appl. No. 10/943,386, Angros, Final Office Action dated Oct. 1, 2009.
U.S. Appl. No. 10/943,386, Angros, Notice of Allowance dated Oct. 2, 2009.
U.S. Appl. No. 10/943,386, Angros, C omments on Notice of Allowance dated Oct. 14, 2009.
U.S. Appl. No. 10/943,394, Angros, Office Action Restriction dated Apr. 9, 2007.
U.S. Appl. No. 10/943,394, Angros, Response to Office Action Restriction filed Jul. 9, 2007.
U.S. Serial No. 10/943,394, Angros, Second Preliminary Amendment filed Sep. 5, 2007.
U.S. Appl. No. 10/943,394, Angros, Office Action dated Oct. 10, 2007.
U.S. Appl. No. 10/943,394, Angros, Response to Office Action filed Oct. 25, 2007.
U.S. Appl. No. 10/943,394, Angros, Office Action dated Feb. 22, 2008.
U.S. Appl. No. 10/943,394, Angros, Examiner Interview dated May 8, 2008.
U.S. Appl. No. 10/943,394, Angros, Response to Office Action filed May 30, 2008.
U.S. Appl. No. 10/943,394, Angros, Second Amendment and Response to Office Action filed Aug. 14, 2008.
U.S. Appl. No. 10/943,394, Angros, Third Amendment and Response to Office Action filed Aug. 18, 2008.
U.S. Appl. No. 10/943,394, Angros, Office Action Restriction dated Apr. 27, 2009.
U.S. Appl. No. 10/943,394, Angros, Amendment and Response to Office Action filed Jun. 26, 2009.
U.S. Appl. No. 10/943,394, Angros, Submission of Terminal Disclaimer filed Sep. 15, 2009.
U.S. Appl. No. 10/943,394, Angros, Final Office Action dated Sep. 16, 2009.
U.S. Appl. No. 10/943,394, Angros, Submission of Terminal Disclaimer in Response to Final Office Action filed Sep. 16, 2009.
U.S. Appl. No. 10/943,394, Angros, Notice of Allowance dated Oct. 6, 2009.
U.S. Appl. No. 10/943,394, Angros, Amendment and Comments of Notice of Allowance dated Oct. 14, 2009.
U.S. Appl. No. 10/943,546, Angros, Office Action dated Aug. 27, 2007.
U.S. Appl. No. 10/943,546, Angros, Amendment and Response to Office Action filed Feb. 27, 2008.
U.S. Appl. No. 10/943,546, Angros, Interview Summary Mar. 4, 2008.
U.S. Appl. No. 10/943,546, Angros, Notice of Non-Compliance dated Mar. 10, 2008.
U.S. Appl. No. 10/943,546, Angros, Notice of Allowance dated Mar. 18, 2008.
U.S. Appl. No. 10/943,546, Angros, Response to Interview Summary and Response to Notice of Non-Compliance filed Mar. 26, 2008 (mis-dated Feb. 27, 2008).
U.S. Serial No. 10/943,546, Angros, Request for Continued Examination and Request for Withdrawal of Issuance filed Aug. 15, 2008.
U.S. Appl. No. 10/943,546, Angros, Notice of Allowance dated Aug. 29, 2008.
U.S. Serial No. 10/943,546, Angros, Amendment and Request for Continued Examination filed Sep. 9, 2008.

(56) References Cited

OTHER PUBLICATIONS

U.S. Appl. No. 10/943,546, Angros, Notice of Allowance dated Sep. 22, 2008.
U.S. Appl. No. 11/807,841, Angros, Preliminary Amendment dated Nov. 13, 2007.
U.S. Appl. No. 11/807,841, Angros, Preliminary Amendment dated Aug. 29, 2008.
U.S. Appl. No. 11/807,841, Angros, Office Action Restriction dated Oct. 20, 2008.
U.S. Appl. No. 11/807,841, Angros, Response to Office Action Restriction filed Dec. 18, 2008.
U.S. Appl. No. 11/807,841, Angros, Office Action dated Mar. 30, 2009.
U.S. Appl. No. 11/807,841, Angros, Express Abandonment, filed Jun. 30, 2009.
EP 00947135.0, Angros, Voluntary Amendment Apr. 3, 2002.
EP 00947135.0, Angros, Office Action Jan. 19, 2006.
EP 00947135.0, Angros, Response to Office Action Jul. 28, 2006.
EP 00947135.0, Angros, Office Action Aug. 23, 2006.
EP 00947135.0, Angros, Response to Office Action Nov. 22, 2007.
EP 00947135.0, Angros, Office Action Jun. 14, 2007.
EP 00947135.0, Angros, EP Notice Jan. 28, 2008.
EP 00947135.0, Angros, Response to Office Action and Notice Apr. 3, 2008.
EP 00947135.0, Angros, Second Amendment May 20, 2008.
EP 00947135.0, Angros, Office Action Jun. 19, 2008.
EP 00947135.0, Angros, Response to Office Action Dec. 24, 2008.
EP 00947135.0, Angros, Office Action Jan. 19, 2011.
EP 00947135.0, Angros, Response to Office Action Jul. 19, 2011.
CA 2,379,410, Angros, Office Action Apr. 2, 2008.
CA 2,379,410, Angros, Response to Office Action Oct. 2, 2008.
CA 2,379,410, Angros, Office Action Mar. 12, 2009.
CA 2,379,410, Angros, Response to Office Action Sep. 14, 2009.
CA 2,379,410, Angros, Office Action Jun. 27, 2011.
CA 2,379,410, Angros, Response to Office Action, filed Dec. 22, 2011.
CA 2,379,410, Angros, Office Action, dated Oct. 12, 2012.
U.S. Appl. No. 12/198,692, Angros, Office Action dated Dec. 24, 2009.
U.S. Appl. No. 12/198,692, Angros, Amendment and Response filed Jun. 24, 2010.
U.S. Appl. No. 12/198,692, Angros, Final Office Action dated Sep. 9, 2010.
U.S. Appl. No. 12/198,692, Angros, Interview Summary dated Jan. 21, 2011.
U.S. Appl. No. 12/198,692, Angros, Amendment and Response and Request for Continued Examination filed Jan. 28, 2011.
U.S. Appl. No. 12/198,692, Angros, Response to Interview Summary filed Feb. 8, 2011.
U.S. Appl. No. 12/198,692, Angros, Office Action dated Mar. 18, 2011.
U.S. Appl. No. 12/198,692, Angros, Amendment and Response, filed Apr. 18, 2011.
U.S. Appl. No. 12/198,692, Angros, Notice of Allowance, mailed Jun. 6, 2011.
U.S. Appl. No. 12/561,568, Angros, Office Action dated Jan. 5, 2010.
U.S. Appl. No. 12/561,568, Angros, Amendment and Response filed Jun. 24, 2010.
U.S. Appl. No. 12/561,568, Angros, Supplemental Amendment and Response filed Jun. 25, 2010.
U.S. Appl. No. 12/561,568, Angros, Office Action dated Aug. 25, 2010.
U.S. Appl. No. 12/561,568, Angros, Amendment and Response and Request for Continued Examination filed Feb. 24, 2011.
U.S. Appl. No. 12/561,568, Angros, Office Action dated Mar. 10, 2011.
U.S. Appl. No. 12/561,568, Angros, Amendment and Response, filed Apr. 18, 2011.
U.S. Appl. No. 12/561,568, Angros, Notice of Allowance, mailed Jun. 2, 2011.
U.S. Appl. No. 12/495,152, Angros, Preliminary Amendment filed Jul. 16, 2009.
U.S. Appl. No. 12/495,152, Angros, Office Action dated Jan. 14, 2011.
U.S. Appl. No. 12/495,152, Angros, Amendment and Response, filed May 10, 2011.
U.S. Appl. No. 12/495,152, Angros, Notice of Allowance, mailed Jul. 18, 2011.
U.S. Appl. No. 12/495,152, Angros, Amendment under 37 CFR 1.312, filed Sep. 13, 2011.
U.S. Appl. No. 12/495,152, Angros, PTO Response to Rule 312 Communication, mailed Sep. 22, 2011.
U.S. Appl. No. 12/624,097, Angros, Office Action dated Oct. 4, 2010.
U.S. Appl. No. 12/624,097, Angros, Amendment and Response, filed Apr. 4, 2011.
U.S. Appl. No. 12/624,097, Angros, Office Action Aug. 31, 2011.
U.S. Appl. No. 12/624,097, Angros, Response to Office Action, filed Sep. 23, 2011.
U.S. Appl. No. 12/624,097, Angros, Notice of Allowance, mailed Nov. 29, 2011.
U.S. Appl. No. 12/624,120, Angros, Office Action dated Oct. 1, 2010.
U.S. Appl. No. 12/624,120, Angros, Amendment and Response filed Mar. 29, 2011.
U.S. Appl. No. 12/624,120, Angros, Office Action Aug. 15, 2011.
U.S. Appl. No. 12/624,120, Angros, Response to Office Action, filed Aug. 26, 2011.
U.S. Appl. No. 12/624,120, Angros, Further Remarks, filed Sep. 2, 2011.
U.S. Appl. No. 12/624,120, Angros, Notice of Allowance Oct. 6, 2011.
U.S. Appl. No. 13/220,438, Angros, Preliminary Remarks, filed Aug. 29, 2011.
U.S. Appl. No. 13/220,438, Angros, Office Action dated Feb. 21, 2012.
U.S. Appl. No. 13/220,438, Angros, Response to Office Action, filed Jul. 20, 2012.
U.S. Appl. No. 13/220,438, Angros, Notice of Allowance, dated Jul. 25, 2012.
U.S. Appl. No. 13/220,438, Angros, Applicant-Initiated Interview Summary, dated Aug. 1, 2012.
U.S. Appl. No. 13/220,438, Angros, 312 Amendment, filed Sep. 27, 2012.
U.S. Appl. No. 13/220,438, Angros, PTO Response to 312 Amendment, dated Aug. 1, 2012.
U.S. Appl. No. 13/220,454, Angros, Preliminary Remarks, filed Aug. 29, 2011.
U.S. Appl. No. 13/220,454, Angros, Office Action, mailed Feb. 28, 2012.
U.S. Appl. No. 13/220,454, Angros, Response to Office Action, filed Jul. 20, 2012.
U.S. Appl. No. 13/220,454, Angros, Applicant-Initiated Interview Summary, dated Aug. 2, 2012.
U.S. Appl. No. 13/220,454, Angros, Notice of Allowance, dated Aug. 6, 2012.
U.S. Appl. No. 13/220,454, Angros, 312 Amendment, filed Sep. 27, 2012.
U.S. Appl. No. 13/220,454, Angros, PTO Response to 312 Amendment, dated Oct. 11, 2012.
U.S. Appl. No. 13/291,521, Angros, Preliminary Remarks, filed Nov. 8, 2011.
U.S. Appl. No. 13/311,066, Angros, Preliminary Amendment, filed Dec. 5, 2011.
U.S. Appl. No. 13/311,066, Angros, Office Action, dated Mar. 28, 2012.
U.S. Appl. No. 13/311,066, Angros, Amendment and Response to Office Action, mailed Jul. 20, 2012.
U.S. Appl. No. 13/311,066, Angros, Notice of Allowance, dated Sep. 21, 2012.

IN SITU HEAT INDUCED ANTIGEN RECOVERY AND STAINING APPARATUS AND METHOD

CROSS-REFERENCE TO RELATED APPLICATIONS

This application is a continuation of U.S. Ser. No. 13/742,174, filed Jan. 15, 2013, which is a continuation of U.S. Ser. No. 13/311,066, filed Dec. 5, 2011, now U.S. Pat. No. 8,354,058, which is a continuation of U.S. Ser. No. 12/624,120, filed Nov. 23, 2009, now U.S. Pat. No. 8,071,023, which is a continuation of U.S. Ser. No. 10/943,394, filed Sep. 17, 2004, now U.S. Pat. No. 7,632,461, which is a continuation of U.S. Ser. No. 10/388,710, filed Mar. 14, 2003, now U.S. Pat. No. 6,855,292, which is a continuation of U.S. Ser. No. 09/612,605, filed Jul. 7, 2000, now U.S. Pat. No. 6,534,008, which claims the benefit of U.S. Provisional Application Ser. No. 60/142,789, filed Jul. 8, 1999, each of which is hereby incorporated herein in its entirety.

BACKGROUND

The present invention is related to the field of treating samples on microscope slides and more specifically to the field of heat induced antigen recovery and staining.

Antigen recovery, also known as antigen unmasking, antigen epitope unmasking, antigen retrieval or heat induced epitope recovery (HIER) is a process in which biological samples (e.g., cells, tissues, blood, fluids) are treated under heat with a series of aqueous or non-aqueous reagents and buffers (e.g., citrate, EDTA, and urea) for the purpose of exposing the presence of specific types of antigens or biochemical features in the biological samples. HIER is regarded as a pre-treatment procedure to be performed prior to the beginning of a specific staining protocol to identify cellular components.

Biological samples must be preserved after removal from the body. This preservation process, known as fixation, kills and localizes the biological material. One of the most common fixatives used widely in the preservation of biological materials is formalin, a 10% aqueous solution of formaldehyde. This fixative, along with other widely utilized fixatives, produces a cross-linking network around specific sites in the biological material. These sites are known as antigens, and during the fixation process become "masked," by the fixative and thus "invisible" to detection by certain stains. HIER is used as a pre-treatment process to "unmask," "retrieve" or "recover." This process is usually conducted on formalin fixed paraffin embedded tissue sections or cellular preparations mounted on microscope slides.

U.S. Pat. No. 5,244,787 teaches a process of antigen retrieval wherein one or more slides are placed in an aqueous solution within a microwave oven and heated to boiling or near-boiling temperatures. These slides are all treated together in a rack that has been placed in a bath of the solution. The slides are near boiling temperatures for 5-30 minutes, generally around 10 minutes. Due to excessive evaporation from the bath, the patent teaches that the solution should not drop below the biological sample on the slide because drying out of the sample is deleterious. This process further teaches that after boiling or near-boiling for several minutes, usually 5 minutes, one may have to add more solution to the container to prevent the solution from excessive evaporation and subsequent exposure of the samples on the slides. After the addition of more liquid, the process is continued until the desired time is completed. The disclosure of U.S. Pat. No. 5,244,787 is limited to the use of a microwave oven as the source of heating. More recent advances, which have been published, include the use of different types of heating devices such as electric pressure cookers, electric steamers, electric conduction heating surfaces utilizing pressure cookers, steamers, and also steam driving autoclaves (J. of Pathology, 179:347-352, 1996; Biotechnic & Histochemistry, 71(5):263-270, 1996; Biotechnic & Histochemistry, 71(4):190-195, 1996; J. of Histochemistry & Cytochemistry, 45(3): 327-342, 1997).

Although these published methodologies treat the biological sample with different types of solutions and with varying types of chemicals and at different pH's, all teach that all slides are treated together in a bath of the heated solution. After the slides have cooled for a period of time, they are removed from the heating device and they are transferred to another apparatus where they are manually or automatically stained using various reagents. This pre-treatment process of heating and removing the slides from the heating device for staining in a separated apparatus is highly cumbersome and inefficient. The only automated HIER or antigen retrieval instrument available is the BIOGENEX i1000. This instrument, however, still employs the use of the known technology of treating the slides as a group in a container filled with heated solutions. A technician must still remove the slides from the antigen retrieval (heating) instrument and place them in an automated stainer instrument to complete the required staining protocol.

As noted herein, no currently available automated or semi-automated staining instruments specifically teach the ability to heat an aqueous or non-aqueous liquid for the unmasking of antigens. The instruments that do automated or semi-automated staining limit their scope to that task alone, and don't address the task of HIER or antigen retrieval pre-treatments. U.S. Pat. Nos. 5,073,504 and 4,847,208 teach use of a chamber for enclosing and staining a microscope slide but neither teaches use of a heating device to boil a liquid and the user must add the primary antibody manually through a hinged door on top of the chamber. U.S. Pat. Nos. 4,777,020; 4,798,706; and 4,801,431 teach use of a vertical staining "capillary gap" methodology wherein two special slides placed front to front causing an air gap through which liquids are drawn by capillary movement. This gap can only hold a small volume (approx. 300 microliters) of liquid. If heated to near boiling conditions the liquid would evaporate through all four open sides, immediately causing the biological sample to dry. This end result is true also for another capillary gap instrument, shown in U.S. Pat. No. 5,804,141. U.S. Pat. Nos. 5,595,707; 5,654,200; 5,654,199, 5,595,707; and 5,650,327 teach reducing evaporative loss by utilizing an oil layer on top of the aqueous layer. This is somewhat effective in reducing the amount of evaporative loss at 37° C. but the volume of the aqueous layer (approx. 300 microliters) is again minimal, and if heated to boiling, would cause the aqueous layer to dry out leaving only the oil layer present thus damaging the biological sample unless more aqueous reagent was applied during the treatment process. U.S. Pat. No. 5,425,918 also teaches use of small amounts of liquids that are sprayed on the slide and can only heat the slide to 37° C. U.S. Pat. Nos. 5,645,144 and 5,947,167 teach use of an open top chamber present around the slide and use a rotating cover above the slides to reduce evaporation. There is no teaching of high temperature heating of a liquid for a substantial amount of time. Further, even if one would increase the temperature of the slide, the loosely rotating top of the chamber would allow so much evaporative loss that the solution would never reach boiling or near boiling temperatures, nor would it maintain the boiling conditions for 10 minutes or longer. U.S. Pat. No. 5,645,114 teaches use of small volumes of liquids (up to 500 microliters) and has no ability to stop evaporative loss if the slide temperature reaches boiling conditions.

As a result, none of these systems could hold sufficient liquid on top of a slide (e.g., 4 ml) and are enclosed in a chamber which is properly vented to minimize the energy loss from evaporation to cause sufficient heating to boil the liquid on the slide for the length of time generally required to cause antigen unmasking (e.g., 10-30 minutes).

There remains a need for an apparatus which can perform the task of HIER with subsequent staining treatment without the need of switching the slides from one apparatus to another and wherein the treatment of all microscope slides can occur simultaneously thereby increasing efficiency. Of the automated stainers available today, there is not one instrument that has the ability to overcome the inherent problems of heating an aqueous or non-aqueous solution at a sufficient volume without the undesirable effect of evaporative heat loss and subsequent volume decrease of the solution. The negative effects of evaporation are significant. The ability of a liquid to reach boiling or near boiling temperature on a microscope slide is dependent on the containment and control of the steam or vapor generated during the heating process. It is the object of the invention contemplated herein to provide a completely automated HIER apparatus which can recover antigens with multiple types of recovery buffers simultaneously, each specific to its respective microscope slide and which can also be used to stain the microscope slides as well.

DETAILED DESCRIPTION OF THE INVENTION

The present invention is directed to an automated method and apparatus for treating biological samples on microscope slides for unmasking ("retrieving" or "recovering") epitopes or antigens of the biological samples and then staining or otherwise treating the biological samples. The automated apparatus comprises an array of individual reaction compartments, each of which is used to treat a single microscope slide (also referred to herein as a "slide"), wherein each reaction compartment preferably can function and can be controlled independently of the other reaction compartments in the array. Each reaction compartment in the array comprises a support element comprising a surface upon which a microscope slide can be supported and positioned adjacent or inserted into the compartment for treatment with a reagent. The support element further comprises, in a preferred embodiment, a conduction type heating element for heating the microscope slide to a predetermined treatment temperature when desired. The support element with the microscope slide thereon can be raised into or adjacent the reaction compartment for treatment of the microscope slide, or lowered or removed from the reaction compartment for placement of a microscope slide onto or removed from the support surface or for removal of a reagent or rinsing solution from the microscope slide during the treatment process.

Reagents, such as antibodies, enzymes, rinse buffers, antigen recovery buffers, or stains, are contained in an individualized reagent dispensing strip which is specific for each microscope slide to be treated. Since each microscope slide and reaction compartment is generally provided with its own reagent dispensing strip, each microscope slide can be treated independently with a different set of reagents (a particular treatment protocol) while being treated simultaneously with other microscope slides. Similarly, in an especially preferred embodiment of the invention, each microscope slide can be heated separately, as well as treated with a different treatment protocol.

The apparatus of the present invention therefore comprises, in a preferred embodiment, a plurality of individualized reaction compartments in a chamber which can be substantially closed for minimizing evaporation during heating. A microscope slide can be supported in each reaction compartment, and each microscope slide can be heated separately therein. A reagent dispensing strip containing a plurality of individually contained reagents (reagent "bubbles", "blisters" or "capsules") is positioned upon an upper portion of each reaction compartment, and at an appropriate time, a reagent from each reagent dispensing strip is expelled from a reagent capsule under compression and is thereby applied to the biological sample on the microscope slide. Or, a reagent, such as an antigen recovery buffer can be introduced via a separate dispenser. The term "reagent" is defined herein to include any type of fluid material that may be applied to the biological material on the microscope slide, including antibodies, stains, enzymes, buffers, rinses, or washes, or any other material applied in the process of antigen recovery or treating the biological material on the microscope slide to be viewed under the microscope.

During an antigen recovery step, the microscope slide, sample, and antigen recovery buffer thereon are heated to an appropriate temperature for a predetermined duration to cause the antigen recovery buffer to react with the sample on the microscope slide, after which the antigen recovery buffer is removed from the microscope slide, preferably by washing or flooding the microscope slide or chamber containing the microscope slide with a rinse buffer and allowing the rinse buffer to drain off by gravity or by blowing the solution off the microscope slide using pressurized air. Each microscope slide may be treated in the same manner, or may be treated with different reagents using a different treatment protocol, preferably simultaneously, yet independently.

When a reagent is provided via a reagent dispensing strip, the apparatus is preferably equipped with a drive mechanism for causing the reagent dispensing strip to be advanced in a forward direction wherein each reagent capsule in succession is positioned above an aperture in the compartment through which the reagent in the capsule is delivered. The reagent dispensing strip may be advanced using rollers positioned along the upper end of the compartment or a pushing mechanism which pushes upon the rear end of the reagent dispensing strip. The reagent in the reagent capsule of the reagent dispensing strip is to be applied to the microscope slide by a pressing mechanism which, in a preferred version, compresses and thereby crushes the reagent capsule and causes the reagent to be expelled and deposited directly onto the microscope slide.

In a preferred method of the present invention, a plurality of microscope slides, each having thereon a sample to be treated, is provided. Each microscope slide is positioned upon a support element which is then moved into an application position. A plurality of reagent dispensing strips is provided, one for each microscope slide to be treated. Each microscope slide is subjected to an antigen recovery step then is treated by applying a reagent from its corresponding reagent dispensing strip. Each microscope slide can be handled differently, if desired, during the treatment cycle. After a predetermined duration, the microscope slide and support element is moved to a removal position wherein the reagent is removed, preferably in between reagent applications, by treatment with a rinsing solution to remove the reagent prior to further treatment. Each microscope slide can be treated according to the treatment protocol specific to that sample or that particular microscope slide. All microscope slides may be treated using the same protocol, or one or more, or all, of the microscope slides may be treated using a different protocol.

An example of a treatment protocol comprises:
1) antigen recovery, 10 minutes at 98° C.,
2) cool, 20 minutes,
3) rinse buffer,
4) primary antibody, 30 minutes,
5) rinse,
6) biotinylated linking antibody, 10 minutes,
7) rinse buffer,
8) peroxidase labeled streptavidin label,
9) rinse buffer,
10) 3,3'-diaminobenzidine chromogen,
11) rinse buffer,
12) chromogen enhancer,
13) rinse buffer, and
14) counter stain.

A variety of other treatment protocols are well known to those of ordinary skill in the art and further discussion of them herein is not deemed necessary. Each microscope slide, if necessary, may be heated prior to application of the reagent, if necessary, then may be cooled as the reagent is removed, then reheated, if necessary, prior to or after addition of the next reagent. The entire process is run automatically once the microscope slide is disposed onto the support element, and the reagent dispensing strip is positioned upon the upper side of the reaction compartment.

Turning now to the drawings, a specific embodiment of the apparatus of the present invention is shown in FIGS. 1-6. Although FIGS. 1-6 show a preferred version of the invention, it will be understood that the embodiment shown in FIGS. 1-6 is but one of many possible versions of the apparatus enabled herein which will come to the mind of a person of ordinary skill in the art.

Figure 1:
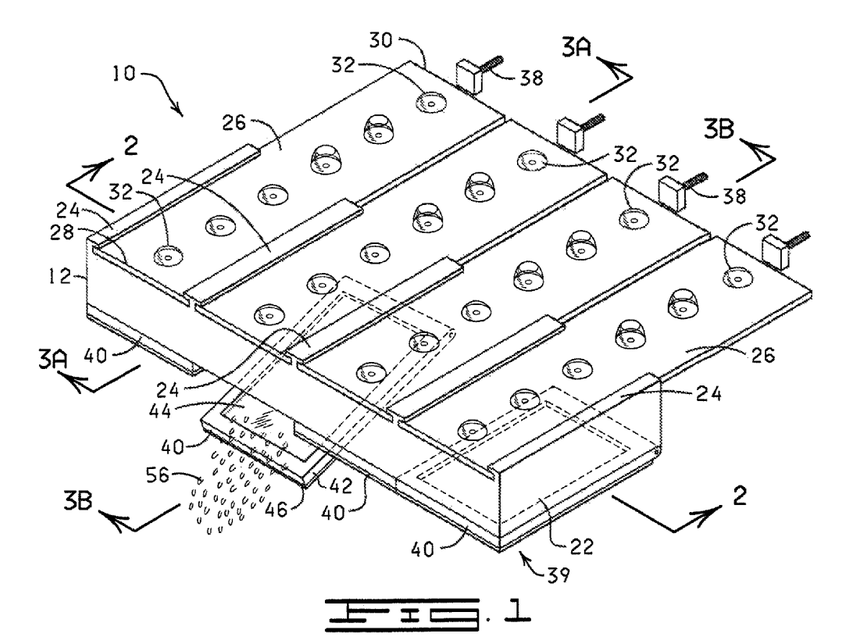
FIG. 1 is a perspective view of an apparatus of the invention (shown without a pressing element for crushing a reagent capsule).
Figure 2:
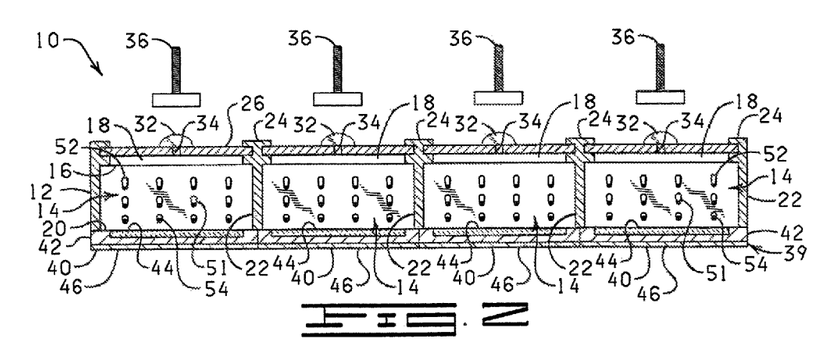
FIG. 2 is a cross-sectional view of the apparatus of FIG. 1 (shown with a pressing element for crushing a reagent capsule).

Shown in FIG. 1, and designated therein by the general reference numeral 10 is an antigen recovery and staining apparatus constructed in accordance with the present invention. The antigen recovery and staining apparatus 10 comprises a treatment chamber 12 which further comprises a plurality of reaction compartments 14 (see FIGS. 2-4). Preferably the treatment chamber 12 generally comprises from 10 to 20 reaction compartments 14 but may contain more or fewer. Each reaction compartment 14, when enclosed, minimizes evaporation of a reagent solution when a microscope slide is exposed to high temperature pretreatment conditions. Each reaction compartment 14 has an upper side 16 having an opening 18 therein, a lower side 20, and a pair of sidewalls 22 which extend from the rear end 23a of the treatment chamber 12 to the front end 23b of the treatment chamber 12. Positioned above each reaction compartment 14 is a reagent dispensing strip holder 24 for holding and guiding a reagent dispensing strip 26 (see FIGS. 5 and 6). Each reagent dispensing strip 26 has a front end 28 and a rear end 30 and a plurality of capsules 32 made of a crushable plastic material such as polyethylene or another suitable material (e.g., polypropylene or polystyrene) and which may include one or more multiple capsules 32a. The size of each capsule 32 or multiple capsule 32a may be adjusted to accommodate the amount of reagent which is desired to be applied to a microscope slide 44. Each capsule 32 or multiple capsule 32a contains a reagent or treatment solution which is intended to be applied to a biological material on the microscope slide 44. Multiple capsule 32a is useful in a method wherein two or more reagents must be contained separately before being applied to the microscope slide 44. When the multiple capsule 32a is crushed by the pressing mechanism 36, two or more reagents contained within the capsule 32a are combined and simultaneously applied to the microscope slide 44.

Figure 3A:
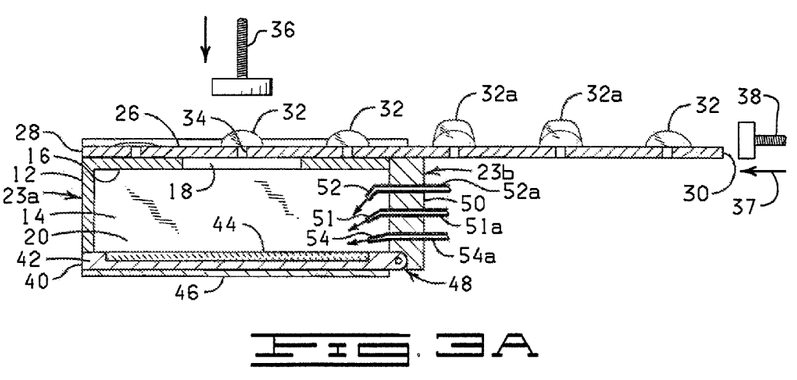
FIG. 3A is a cross-sectional view of the apparatus of FIG. 1 (shown with a reaction compartment having a raised slide support surface) taken through line 3A-3A.
Figure 3B:
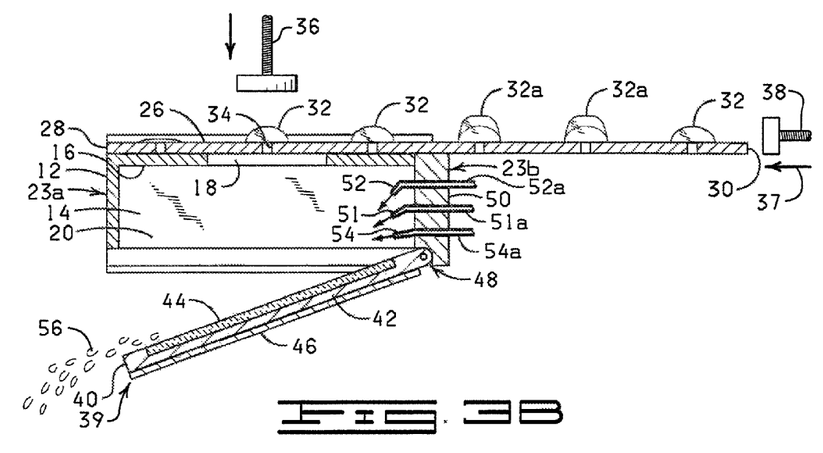
FIG. 3B is a cross-sectional view of the apparatus of FIG. 1 (shown with a reaction compartment having a lowered slide support surface) taken through line 3B-3B.

Other embodiments of the reagent dispensing strip 26 and the reagent capsule 32 and multiple capsule 32a will readily be apparent to one of ordinarily skill in the art. For example, each reagent dispensing strip 26 may comprise a one or more "blank" spaces for insertion of individualized capsules 32 by a user. Below each capsule 32 or multiple capsule 32a is an aperture or weak area 34 in the reagent dispensing strip 26 through which the reagent in the capsule 32 or multiple capsules 32 can be forced by a pressing mechanism 36. The "blank" space or space left by the puncturing of a capsule 32 or 32a, or vents in the reagent dispensing strip 26 may function to release pressure, steam or vapors produced during the treatment process. The reagent dispensing strip 26 is advanced in a direction 37 toward the front end 23b of the treatment chamber 12 by a reagent strip drive mechanism 38 driven, for example, by an electric motor which in FIGS. 1, 3A and 3B is shown as a pushing mechanism comprising a threaded shaft, but which may instead by a mechanism (not shown) comprising rollers which drive, draw or "pull" the reagent strip holder 24 in a forward direction 37.

Figure 4:
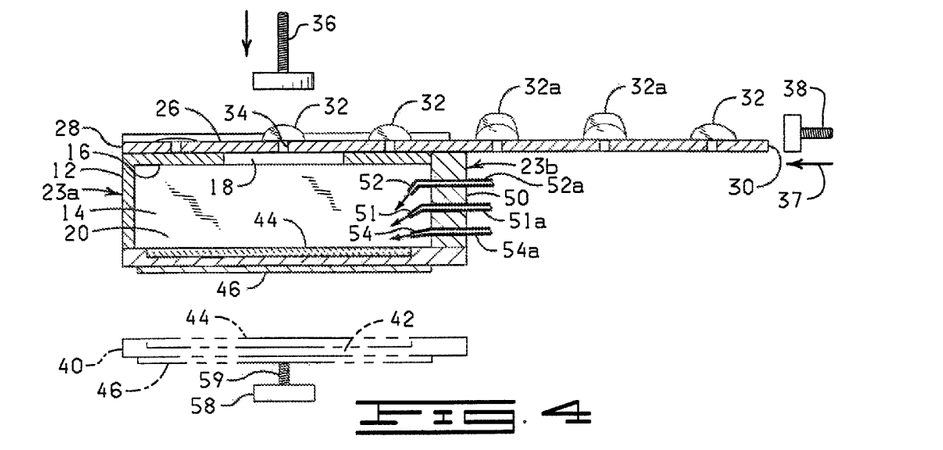
FIG. 4 is a cross-sectional view of an alternative embodiment of the apparatus of the present invention having an alternate type of slide support surface.
Figure 5:
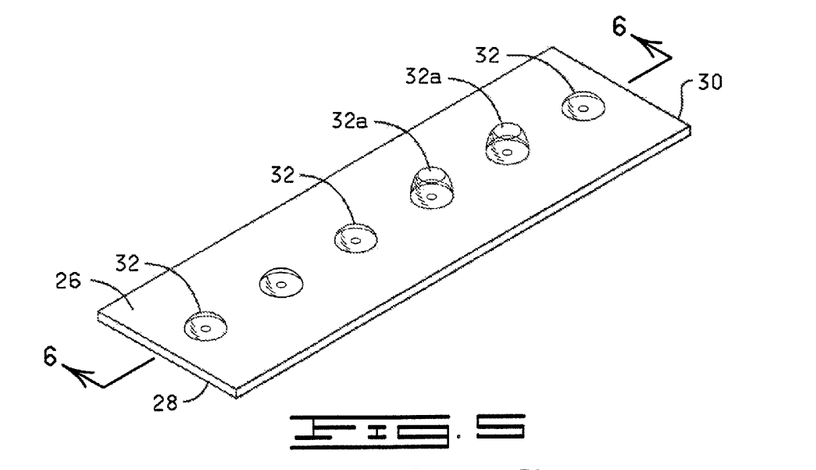
FIG. 5 is a perspective view of a reagent strip of the present invention.
Figure 6:
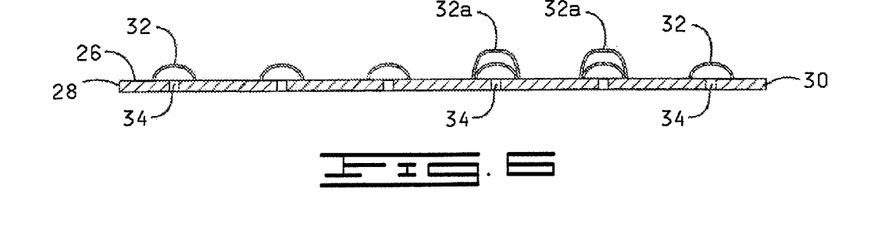
FIG. 6 is a cross-sectional view of the reagent strip of FIG. 5 taken through the line 6-6.
Figure 9:
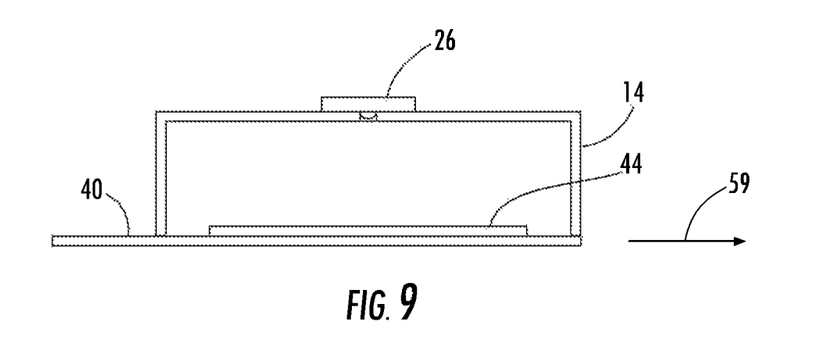
FIG. 9 is a cross-sectional view of an alternative embodiment of the apparatus showing a slide support element which is movable in a horizontal direction.

Each reaction compartment 14 further comprises at its lower side 20 a slide support element 40 having a slide tray 42 upon which the microscope slide 44 can be positioned and held for treatment. The slide support elements 40 together comprise a slide support assembly 39. With the microscope slide 44 disposed on the slide support element 40, the slide support element 40 and the microscope slide 44 are positioned in an application position to fit adjacent the lower side 20 of the reaction compartment 14, thereby constituting an openable bottom of the reaction compartment 14. The slide support element 40 further has a heating element 46 incorporated therein for heating the microscope slide 44 as discussed elsewhere herein. In one embodiment, the slide support element 40 has a hinge 48 for enabling the slide support element 40 to be moved (raised) into an application position (FIG. 3A) and therefrom lowered (e.g., tilted) into an opened position (see FIG. 3B). Alternatively, the slide support element 40 may be raised and lowered into position by another mechanism, such as a stepper motor 58 and screw drive 59 mechanism (FIG. 4). Alternatively, as indicated in FIG. 9, the slide support element 40 may be moved in a manner like the movement of a CD ROM drive door on a computer wherein the slide support element 40, and the microscope slide 44 placed thereon, is made to slidingly move horizontally into the reaction compartment 14 in a single back and forth direction as indicated by arrow 59. In the reaction compartment 14, the microscope slide 44 on the slide support element 40 is positioned to receive a reagent from a reagent dispensing strip 26. Each reaction compartment 14 further comprises a manifold 50 (FIGS. 3A-4) which comprises, in a preferred embodiment, a plurality of reagent dispensing ports or elements including, for example but not limited to, an antigen recovery buffer dispenser 51 connected via an antigen recovery buffer supply line 51a to an antigen recovery buffer supply (not shown), a rinse buffer dispenser 52 connected via a rinse buffer supply line 52a to a rinse buffer supply (not shown) and an air pressure nozzle (pressurized air nozzle) 54 connected via an air line 54a to an air supply (not shown). The antigen recovery buffer dispenser 51 applies an antigen recovery buffer to the microscope slide 44 for the antigen recovery treatment step prior to staining or other preparation of the biological material on the microscope slide 44. The rinse buffer dispenser 52 applies a rinse buffer 56 to the microscope slide 44 to rinse a reagent from the microscope slide 44. The air pressure nozzle (pressurized air nozzle) 54 functions to clear away a rinse buffer 56 from the microscope slide 44. Dispensers 51 and 52 may be used to dispense other reagents, and may constitute more than, or fewer than, the dispensers shown in FIGS. 2, 3A, 3B, and 4. The microscope slide 44 is generally disposed in a removal position for facilitating removal of the rinse buffer 56 as shown in FIGS. 1 and 3B. Each slide support element 40, in a preferred embodiment, can be heated or moved independently of any other slide support element 40, although one of ordinary skill in the art can envision that the slide support elements 40 may be designed to operate in concert, i.e., simultaneously. Each reaction compartment 14 preferably can contain a volume of up to 15 ml.

The antigen recovery and staining apparatus 10 can be controlled automatically wherein predetermined sequences and operations are carried out using various electromechanical systems which are not shown but which are well known to those of ordinary skill in the art. For example, each of the steps of raising into a treatment position and lowering into a removal position each of the slide support elements 40, applying an antigen recovery buffer, advancing each reagent dispensing strip 26, compressing each capsule 32 or 32a of the reagent dispensing strip 26, heating each microscope slide 44 on the slide support surface 40, applying a rinse buffer 56 to the microscope slide 44, removing the rinse buffer 56 or other reagent from the microscope slide 44, and treating each microscope slide 44 independently can be automatically controlled and programmed using programming methods and devices well known in the art. Because each reaction compartment 14 and slide support element 40 can be controlled independently, a microscope slide 44 can even be removed or inserted even while other reaction compartments 14 are in operation.

Figure 10:
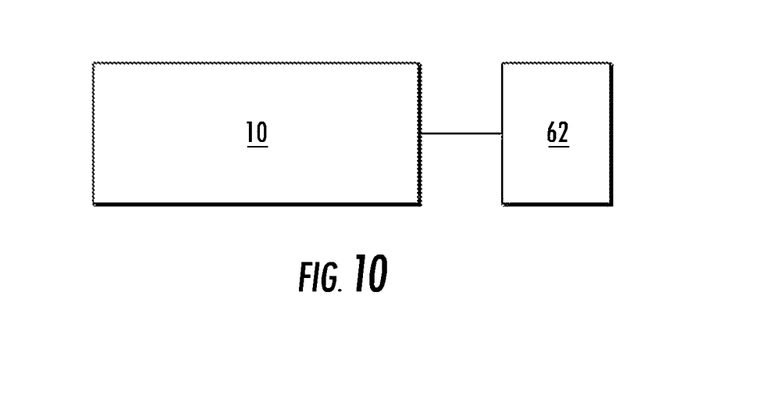
FIG. 10 is a schematic view of an apparatus of the invention and a microprocessor which controls the apparatus.

Preferably, a microprocessor 62, controls the antigen recovery and staining apparatus 10 as shown in FIG. 10. That is, an operator programs the microprocessor 62 with information such as which reaction compartments 14 are to be used and to what temperature each is to be heated and at which steps, then programs the particular treatment protocol to be performed on the sample on each microscope slide 44 on each slide support element 40. Variables in these protocols can include the particular type of reagent dispensing strip 26 to be used, the time that each reagent or treatment solution on the reagent dispensing strip 26 will be allowed to react with the sample on the microscope slide 44, whether the microscope slide 44 will be heated, and if so to what temperature and for how long, and the manner in which the microscope slide 44 will be rinsed, for example. Other variables not listed herein may also be programmed.

Figure 7:
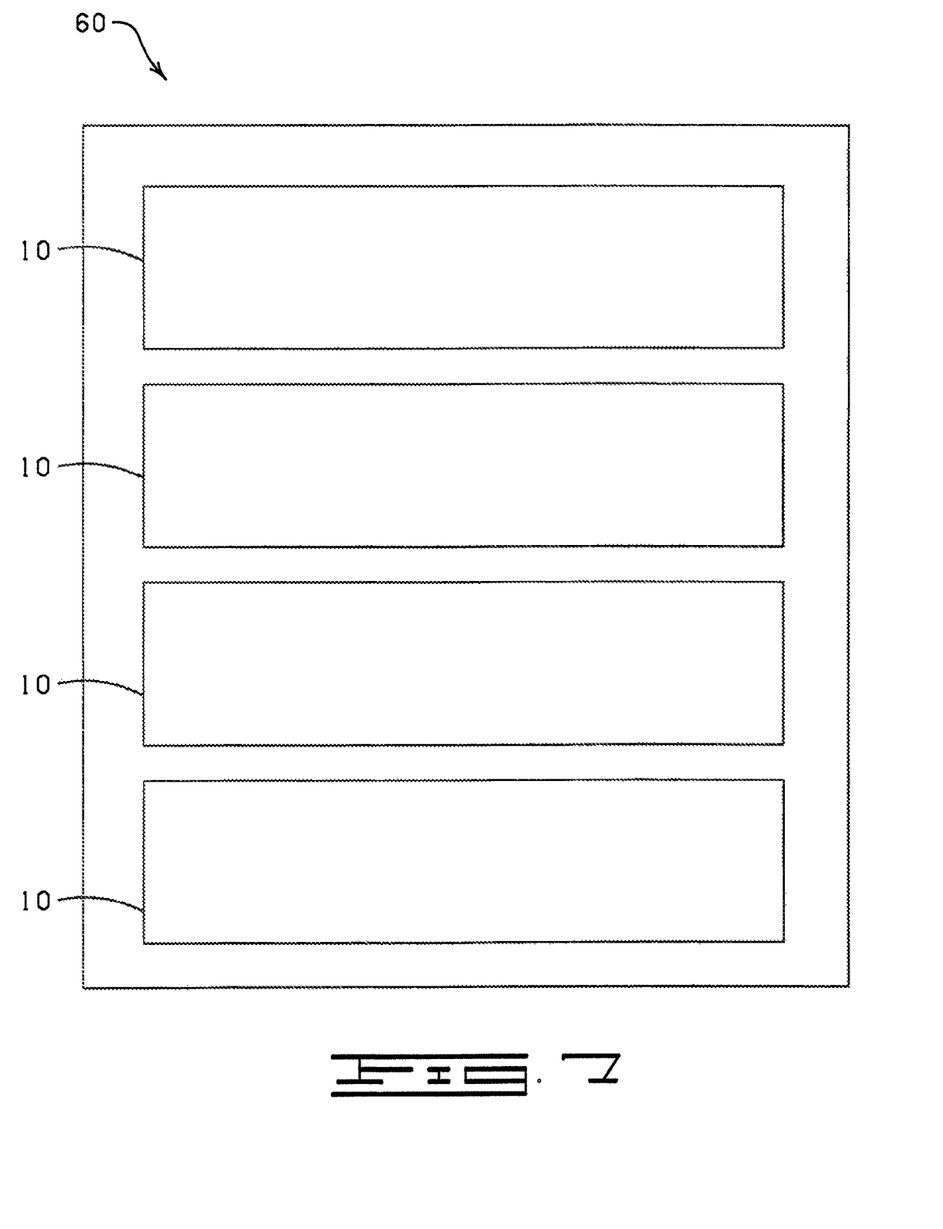
FIG. 7 is an elevational view of a modular apparatus containing a plurality of the apparatus of FIG. 1.

The invention may further comprise a modular apparatus 60 comprising a plurality of antigen recovery and staining apparatuses 10 each serving as an individual module in the modular apparatus 60. The individual modules can be "stacked" together for example, as shown in FIG. 7, or may be oriented in any other desirable manner.

Figure 8:
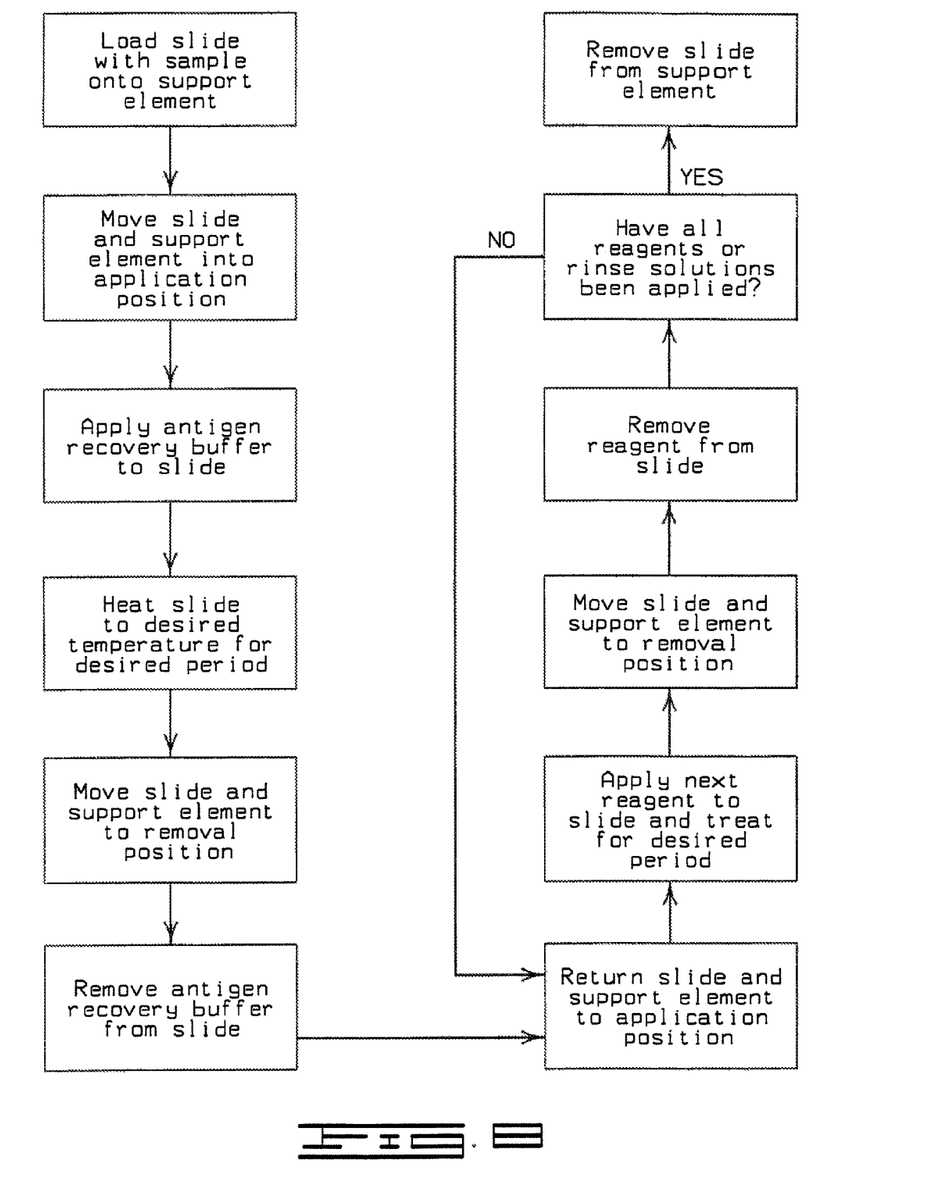
FIG. 8 is a flow chart showing a preferred sequence of steps in the method of the present invention.

Shown in FIG. 8 is a schematic drawing which describes the preferred method of the present invention. In the first step, a microscope slide 44 which has a sample disposed thereon is provided, and is disposed onto a slide support element 40 which is moved into an application or treatment position adjacent or against the reaction compartment 14. If a plurality of microscope slides 44 is supplied, each microscope slide 44 is disposed on a separate microscope slide support element 40 and the microscope slides 44 are moved independently or simultaneously into an application position.

Once in the application position, an antigen recovery buffer is initially applied to the sample on the microscope slide 44. Microscope slide 44 is then heated to a desired, predetermined temperature, for example from about 120° C. to about 160° C. whereby the antigen recovery buffer is heated to a temperature of from about 90° C. to 100° C., for example. The microscope slide 44 is allowed to react with the reagent for a predetermined length of time, for example, 10 to 30 minutes, preferably at 95°-98° C. Venting of steam may occur through small holes (not shown) in the reagent strip 26 or elsewhere in the reaction compartment 14. Venting may occur through a vapor pressure release device in the reaction compartment 14. It is not necessary to add additional antigen recovery buffer during this step. After the reaction period is over, the slide support element 40 and the microscope slide 44 thereon are moved (lowered or dropped) to a removal position, if necessary, where the antigen recovery buffer is removed from the microscope slide 44, for example, by applying a rinsing solution or buffer to the microscope slide 44 or by gravity or by pressurized air. A rinse solution or buffer may be applied and removed more than once for treatment or for removal of a particular reagent before or after lowering the microscope slide 44 to the removal position. It may be desirable to add rinse buffer to the microscope slide 44 to cool the microscope slide 44 prior to lowering the microscope slide 44 to the removal position, for example, by adding rinse buffer 56 to the antigen recovery buffer before the microscope slide 44 is moved to the removal position. After the microscope slide 44 has been treated for antigen recovery, another reagent can then be applied for treatment of the sample on the microscope slide 44. In this step, the microscope slide 44 and slide support element 40 are then returned to the application position, a reagent is applied, and is then removed after the treatment period. The series of steps may be repeated. When the treatment of the sample is completed, the microscope slide 44 is removed from the slide support element 40 for further treatment or analysis apart from the antigen recovery and staining apparatus 10.

Changes may be made in the construction and the operation of the various components, elements and assemblies described herein or in the steps or the sequence of steps of the methods described herein without departing from the scope of the invention as defined in the following claims.

What is claimed is:

1. A method of treating biological samples, comprising:
   placing a first microscope slide in a horizontal position on a first slide support element with the first microscope slide having a first biological sample disposed thereon;
   placing a second microscope slide in a horizontal position on a second slide support element with the second microscope slide having a second biological sample disposed thereon;
   horizontally moving the first slide support into a treatment chamber of an antigen recovery and staining apparatus so as to position the first microscope slide and the first biological sample in the treatment chamber;
   horizontally moving the second slide support into the treatment chamber of the antigen recovery and staining apparatus so as to position the second microscope slide and the second biological sample in the treatment chamber;
   treating the first biological sample by applying a first antigen recovery buffer to the first biological sample, heating the first antigen recovery buffer to a desired temperature for a desired period of time to recover antigens of the first biological sample, and applying additional reagents of a treatment protocol;
   treating the second biological sample by applying a second antigen recovery buffer to the second biological sample, heating the second antigen recovery buffer to a desired temperature for a desired period of time to recover antigens of the second biological sample, and applying additional reagents of another treatment protocol;
   determining if one of the first biological sample and the second biological sample has completed the treatment protocol; and
   removing the microscope slide with the biological sample that has completed the treatment protocol from the treatment chamber while the other biological sample continues to be treated in the treatment chamber,
   wherein the step of removing the microscope slide with the biological sample that has completed the treatment protocol from the treatment chamber comprises the steps of:
      horizontally moving the slide support out of the treatment chamber of the antigen recovery and staining apparatus so as to position the microscope slide with the biological sample that has completed the treatment protocol outside of the treatment chamber; and
      removing the microscope slide with the biological sample that has completed the treatment protocol from the slide support element.

2. The method of claim 1 further comprising the steps of:
   positioning the first biological sample in a first reaction compartment and positioning the second biological sample in a second reaction compartment, wherein the first reaction compartment is separate from the second reaction compartment.

3. The method of claim 2 wherein the step of positioning the first biological sample in the first reaction compartment, the first microscope slide defines a portion of the first reaction compartment, and wherein the step of positioning the second biological sample in the second reaction compartment, the second microscope slide defines a portion of the second reaction compartment.

4. The method of claim 2 wherein the step of positioning the first biological sample in the first reaction compartment, the first slide support element defines a portion of the first reaction compartment, and wherein the step of positioning the second biological sample in the second reaction compartment, the second slide support element defines a portion of the second reaction compartment.

5. The method of claim 1 wherein at least one of the first antigen recovery buffer and the second antigen recovery buffer is aqueous and has a boiling point greater than 100° C.

6. The method of claim 1 wherein at least one of the first antigen recovery buffer and the second antigen recover buffer is non-aqueous.

7. The method of claim 1 further comprising the steps of:
   placing a third microscope slide in a horizontal position on the slide support element from which the microscope slide with the biological sample that has completed the treatment protocol has been removed with the third microscope slide having a third biological sample disposed thereon; and
   horizontally moving the slide support with the third microscope slide positioned thereon into a treatment chamber of an antigen recovery and staining apparatus so as to position the third microscope slide and the third biological sample in the treatment chamber while the other biological sample continues to be treated in the treatment chamber.

8. A method of treating biological samples, comprising:
   placing a first microscope slide in a horizontal position on a first slide support element with the first microscope slide having a first biological sample disposed thereon;
   horizontally moving the first slide support into a treatment chamber of an antigen recovery and staining apparatus so as to position the first microscope slide and the first biological sample in the treatment chamber;
   treating the first biological sample by applying a first antigen recovery buffer to the first biological sample, heating the first antigen recovery buffer to a desired temperature for a desired period of time to recover antigens of the first biological sample, and applying additional reagents of a treatment protocol;
   placing a second microscope slide in a horizontal position on a second slide support element with the second microscope slide having a second biological sample disposed thereon; and
   horizontally moving the second slide support into the treatment chamber of the antigen recovery and staining apparatus so as to position the second microscope slide and the second biological sample in the treatment chamber while the first biological sample continues to be treated in the treatment chamber.

9. The method of claim 8 further comprising the steps of:
   treating the second biological sample by applying a second antigen recovery buffer to the second biological sample, heating the second antigen recovery buffer to a desired temperature for a desired period of time to recover antigens of the second biological sample, and applying additional reagents of another treatment protocol;

determining if one of the first biological sample and the second biological sample has completed the treatment protocol; and removing the microscope slide with the biological sample that has completed the treatment protocol from the treatment chamber while the other biological sample continues to be treated in the treatment chamber, wherein the step of removing the microscope slide with the biological sample that has completed the treatment protocol from the treatment chamber comprises the steps of:

horizontally moving the slide support out of the treatment chamber of the antigen recovery and staining apparatus so as to position the microscope slide with the biological sample that has completed the treatment protocol outside of the treatment chamber; and removing the microscope slide with the biological sample that has completed the treatment protocol from the slide support element.

10. The method of claim 9 wherein at least one of the first antigen recovery buffer and the second antigen recovery buffer is aqueous and has a boiling point greater than 100° C.

11. The method of claim 9 wherein at least one of the first antigen recovery buffer and the second antigen recover buffer is non-aqueous.

12. The method of claim 8 further comprising the steps of:
positioning the first biological sample in a first reaction compartment and positioning the second biological sample in a second reaction compartment,
wherein the first reaction compartment is separate from the second reaction compartment.

13. The method of claim 12 wherein the step of positioning the first biological sample in the first reaction compartment, the first microscope slide defines a portion of the first reaction compartment, and wherein the step of positioning the second biological sample in the second reaction compartment, the second microscope slide defines a portion of the second reaction compartment.

14. The method of claim 12 wherein the step of positioning the first biological sample in the first reaction compartment, the first slide support element defines a portion of the first reaction compartment, and wherein the step of positioning the second biological sample in the second reaction compartment, the second slide support element defines a portion of the second reaction compartment.

15. A method of treating biological samples, comprising:
placing a first microscope slide in a horizontal position on a first slide support element with the first microscope slide having a first biological sample disposed thereon;
placing a second microscope slide in a horizontal position on a second slide support element with the second microscope slide having a second biological sample disposed thereon;
horizontally moving the first slide support into a treatment chamber of an antigen recovery and staining apparatus so as to position the first microscope slide and the first biological sample in the treatment chamber;
horizontally moving the second slide support into the treatment chamber of the antigen recovery and staining apparatus so as to position the second microscope slide and the second biological sample in the treatment chamber;

treating the first biological sample by applying a first antigen recovery buffer to the first biological sample, heating the first antigen recovery buffer to a desired temperature for a desired period of time to recover antigens of the first biological sample, and applying additional reagents of a treatment protocol;

treating the second biological sample by applying a second antigen recovery buffer to the second biological sample, heating the second antigen recovery buffer to a desired temperature for a desired period of time to recover antigens of the second biological sample, and applying additional reagents of another treatment protocol;

determining if one of the first biological sample and the second biological sample has completed the treatment protocol; and horizontally removing the microscope slide with the biological sample that has completed the treatment protocol from the treatment chamber while the other biological sample continues to be treated in the treatment chamber.

16. The method of claim 15 further comprising the steps of:
positioning the first biological sample in a first reaction compartment and positioning the second biological sample in a second reaction compartment,
wherein the first reaction compartment is separate from the second reaction compartment.

17. The method of claim 16 wherein the step of positioning the first biological sample in the first reaction compartment, the first microscope slide defines a portion of the first reaction compartment, and wherein the step of positioning the second biological sample in the second reaction compartment, the second microscope slide defines a portion of the second reaction compartment.

18. The method of claim 16 wherein the step of positioning the first biological sample in the first reaction compartment, the first slide support element defines a portion of the first reaction compartment, and wherein the step of positioning the second biological sample in the second reaction compartment, the second slide support element defines a portion of the second reaction compartment.

19. The method of claim 15 wherein at least one of the first antigen recovery buffer and the second antigen recovery buffer is aqueous and has a boiling point greater than 100° C.

20. The method of claim 15 wherein at least one of the first antigen recovery buffer and the second antigen recover buffer is non-aqueous.

21. A method of treating biological samples, comprising:
placing a first microscope slide on a first slide support element with the first microscope slide having a first biological sample disposed thereon;
placing a second microscope slide on a second slide support element with the second microscope slide having a second biological sample disposed thereon;
horizontally moving the first slide support into an antigen recovery and staining apparatus;
horizontally moving the second slide support into the antigen recovery and staining apparatus;
treating the first biological sample by applying a first antigen recovery buffer to the first biological sample, heating the first antigen recovery buffer to a desired temperature for a desired period of time to recover antigens of the first biological sample, and applying additional reagents of a treatment protocol;

treating the second biological sample by applying a second antigen recovery buffer to the second biological sample, heating the second antigen recovery buffer to a desired temperature for a desired period of time to recover antigens of the second biological sample, and applying additional reagents of another treatment protocol;

determining if one of the first biological sample and the second biological sample has completed the treatment protocol; and removing the microscope slide with the biological sample that has completed the treatment protocol from the antigen recovery and staining apparatus while the other biological sample continues to be treated in the antigen recovery and staining apparatus, wherein the step of removing the microscope slide with the biological sample that has completed the treatment protocol from the antigen recovery and staining apparatus comprises the steps of:

horizontally moving the slide support out of the antigen recovery and staining apparatus so as to position the microscope slide with the biological sample that has completed the treatment protocol outside of the antigen recovery and staining apparatus; and removing the microscope slide with the biological sample that has completed the treatment protocol from the slide support element.

22. The method of claim 21 further comprising the steps of:

positioning the first biological sample in a first reaction compartment and positioning the second biological sample in a second reaction compartment, wherein the first reaction compartment is separate from the second reaction compartment.

23. The method of claim 22 wherein the step of positioning the first biological sample in the first reaction compartment, the first microscope slide defines a portion of the first reaction compartment, and wherein the step of positioning the second biological sample in the second reaction compartment, the second microscope slide defines a portion of the second reaction compartment.

24. The method of claim 22 wherein the step of positioning the first biological sample in the first reaction compartment, the first slide support element defines a portion of the first reaction compartment, and wherein the step of positioning the second biological sample in the second reaction compartment, the second slide support element defines a portion of the second reaction compartment.

25. The method of claim 21 wherein at least one of the first antigen recovery buffer and the second antigen recovery buffer is aqueous and has a boiling point greater than 100° C.

26. The method of claim 21 wherein at least one of the first antigen recovery buffer and the second antigen recover buffer is non-aqueous.

27. The method of claim 21 further comprising the steps of:

placing a third microscope slide in a horizontal position on the slide support element from which the microscope slide with the biological sample that has completed the treatment protocol has been removed with the third microscope slide having a third biological sample disposed thereon; and horizontally moving the slide support with the third microscope slide positioned thereon into the antigen recovery and staining apparatus so as to position the third microscope slide and the third biological sample in the antigen recovery and staining apparatus while the other biological sample continues to be treated in the antigen recovery and staining apparatus.

28. A method of treating biological samples, comprising:

placing a first microscope slide on a first slide support element with the first microscope slide having a first biological sample disposed thereon;

horizontally moving the first slide support an antigen recovery and staining apparatus;

treating the first biological sample by applying a first antigen recovery buffer to the first biological sample, heating the first antigen recovery buffer to a desired temperature for a desired period of time to recover antigens of the first biological sample, and applying additional reagents of a treatment protocol;

placing a second microscope slide on a second slide support element with the second microscope slide having a second biological sample disposed thereon; and horizontally moving the second slide support into the antigen recovery and staining apparatus so as to position the second microscope slide and the second biological sample in the antigen recovery and staining apparatus while the first biological sample continues to be treated in the antigen recovery and staining apparatus.

29. The method of claim 28 further comprising the steps of:

treating the second biological sample by applying a second antigen recovery buffer to the second biological sample, heating the second antigen recovery buffer to a desired temperature for a desired period of time to recover antigens of the second biological sample, and applying additional reagents of another treatment protocol;

determining if one of the first biological sample and the second biological sample has completed the treatment protocol; and removing the microscope slide with the biological sample that has completed the treatment protocol from the treatment chamber while the other biological sample continues to be treated in the treatment chamber, wherein the step of removing the microscope slide with the biological sample that has completed the treatment protocol from the antigen recovery and staining apparatus comprises the steps of:

horizontally moving the slide support out of the antigen recovery and staining apparatus so as to position the microscope slide with the biological sample that has completed the treatment protocol outside of the antigen recovery and staining apparatus; and removing the microscope slide with the biological sample that has completed the treatment protocol from the slide support element.

30. The method of claim 29 wherein at least one of the first antigen recovery buffer and the second antigen recovery buffer is aqueous and has a boiling point greater than 100° C.

31. The method of claim 29 wherein at least one of the first antigen recovery buffer and the second antigen recover buffer is non-aqueous.

32. The method of claim 28 further comprising the steps of:

positioning the first biological sample in a first reaction compartment and positioning the second biological sample in a second reaction compartment, wherein the first reaction compartment is separate from the second reaction compartment.

33. The method of claim 32 wherein the step of positioning the first biological sample in the first reaction compartment, the first microscope slide defines a portion of the first reaction compartment, and wherein the step of positioning the second biological sample in the second reaction compartment, the second microscope slide defines a portion of the second reaction compartment.

34. The method of claim 32 wherein the step of positioning the first biological sample in the first reaction compartment, the first slide support element defines a portion of the first reaction compartment, and wherein the step of positioning the second biological sample in the second reaction compartment, the second slide support element defines a portion of the second reaction compartment.

35. A method of treating biological samples, comprising:
placing a first microscope slide on a first slide support element with the first microscope slide having a first biological sample disposed thereon;
placing a second microscope slide on a second slide support element with the second microscope slide having a second biological sample disposed thereon;
horizontally moving the first slide support into an antigen recovery and staining apparatus;
horizontally moving the second slide support into the antigen recovery and staining apparatus;
treating the first biological sample by applying a first antigen recovery buffer to the first biological sample, heating the first antigen recovery buffer to a desired temperature for a desired period of time to recover antigens of the first biological sample, and applying additional reagents of a treatment protocol;
treating the second biological sample by applying a second antigen recovery buffer to the second biological sample, heating the second antigen recovery buffer to a desired temperature for a desired period of time to recover antigens of the second biological sample, and applying additional reagents of another treatment protocol;
determining if one of the first biological sample and the second biological sample has completed the treatment protocol; and
horizontally removing the microscope slide with the biological sample that has completed the treatment protocol from the antigen recovery and staining apparatus while the other biological sample continues to be treated in the antigen recovery and staining apparatus.

36. The method of claim 35 further comprising the steps of:
positioning the first biological sample in a first reaction compartment and positioning the second biological sample in a second reaction compartment,
wherein the first reaction compartment is separate from the second reaction compartment.

37. The method of claim 36 wherein the step of positioning the first biological sample in the first reaction compartment, the first microscope slide defines a portion of the first reaction compartment, and wherein the step of positioning the second biological sample in the second reaction compartment, the second microscope slide defines a portion of the second reaction compartment.

38. The method of claim 36 wherein the step of positioning the first biological sample in the first reaction compartment, the first slide support element defines a portion of the first reaction compartment, and wherein the step of positioning the second biological sample in the second reaction compartment, the second slide support element defines a portion of the second reaction compartment.

39. The method of claim 35 wherein at least one of the first antigen recovery buffer and the second antigen recovery buffer is aqueous and has a boiling point greater than 100° C.

40. The method of claim 35 wherein at least one of the first antigen recovery buffer and the second antigen recover buffer is non-aqueous.

* * * * *

UNITED STATES PATENT AND TRADEMARK OFFICE
CERTIFICATE OF CORRECTION

PATENT NO.       : 9,464,974 B2                                  Page 1 of 1
APPLICATION NO.  : 14/253555
DATED            : October 11, 2016
INVENTOR(S)      : Lee H. Angros It is certified that error appears in the above-identified patent and that said Letters Patent is hereby corrected as shown below:

In the Claims
Column 14, Line 8: After "support" insert -- into --

Signed and Sealed this
Twenty-eighth Day of February, 2017

Michelle K. Lee
*Director of the United States Patent and Trademark Office*